| United States Patent [19] | [11] Patent Number: 5,030,396 |
| --- | --- |
| Saita et al. | [45] Date of Patent: Jul. 9, 1991 |

[54] PROCESS FOR PRODUCTION OF POROUS CERAMIC ARTICLE

[75] Inventors: Kenji Saita, Toyonaka; Susumu Miyazaki, Ibaraki, both of Japan

[73] Assignee: Sumitomo Chemical Company, Limited, Osaka, Japan

[21] Appl. No.: 396,118

[22] Filed: Aug. 21, 1989

[51] Int. Cl.$^5$ ............................................. B29C 65/00
[52] U.S. Cl. ........................................ 264/44; 264/60
[58] Field of Search .................... 264/59, 60, DIG. 76, 264/62, 109, 44

[56] References Cited

U.S. PATENT DOCUMENTS

| 3,090,094 | 5/1963 | Schwartzwalder et al. | 264/59 |
| 4,034,506 | 7/1977 | Kasahara et al. | 47/64 |
| 4,158,684 | 6/1979 | Klawitter et al. | 264/62 |
| 4,179,485 | 12/1979 | Tritten . | |
| 4,437,191 | 3/1984 | vander Zel et al. | 623/16 |
| 4,697,632 | 10/1987 | Lirones | 264/60 |
| 4,803,025 | 2/1989 | Brockmeyer | 264/59 |

FOREIGN PATENT DOCUMENTS 923862  4/1963  United Kingdom ................. 264/59

*Primary Examiner*—Jan H. Silbaugh
*Assistant Examiner*—Christopher A. Fiorilla
*Attorney, Agent, or Firm*—Birch, Stewart, Kolasch & Birch

[57] ABSTRACT

A process for the production of a ceramic shaped implant having a porous layer with interconnected spherical pores on the surface thereof includes the steps of disposing a porous element having a three dimensionally connected structure made of a heat decomposable material, in which structure, adjacent units share connecting portions and voids, in contact with or adjacent to a ceramic substrate, and filling a space between the ceramic substrate and the porous element and the voids of the porous element with a slurry comprising ceramic powder made from the same material as the ceramic substrate, and then heating to sinter the porous material and the ceramic substrate together.

10 Claims, No Drawings

PROCESS FOR PRODUCTION OF POROUS CERAMIC ARTICLE

BACKGROUND OF THE INVENTION

Field of the Invention

The present invention relates to a process for production of a porous ceramic article. The ceramic article according to the present invention is useful as an implant material for an artificial bone, a prosthetic bone, a filter medium and so on.

Description of the Related Art

A porous ceramic article is used as a ceramic implant material for an artificial dental root, an artificial bone and so one, and the material replaces the hard tissue of the human body since it is excellent in biological compatibility and mechanical strength.

When a bone contacts a porous material having pores of more than 50 $\mu$m in diameter, a newly formed bone cell invades the pore. The porous material having such a larger diameter is poor in the mechanical strength. To overcome this problem, a process for the production of a prosthetic bone article in which a porous material is combined with a metal or dense ceramic material is proposed in Japanese Patent Kokai Publication No. 109407/1974 (hereinafter referred to as "reference 1"). This process comprises heating a ceramic material in the form of granules having a selected size at a temperature lower than a sintering temperature thereof, compressing it under a pressure of about 1 ton/cm$^2$ and sintering to form a porous block. When combined with the metal, the process further comprises disposing the sintered block in a mold and casting the metal to fix the block to a metal rod. When combined with the ceramic material, the process further comprises compressing together the block which has not been sintered and the dense ceramic material in the form of a block produced in a separate step and then sintering to make them integral. It is reported that a radius of the pore of the porous block is in the range of from 100 to 200 $\mu$m and its porosity is 30%. Another process is described in Japanese Utility Model Publication No. 34731/1981 (hereinafter referred to as "reference 2"), in which an implant article for the use in a bone is produced by fixing porous alumina ceramic material around a core rod of single crystalline alumina. This process comprises mixing together ceramic powder and material which may be burnt off, compression molding and then calcining to produce a porous material, which is fixed around an outer shell of a core made of the single crystalline alumina with an adhesive or by screwing. It is reported that a diameter of the pore of the porous material is in the range of 0.2 to 0.7 mm.

In the process described in the reference 1, the compressed block made of the alumina granules having a diameter of in the range of 0.5 to 1.5 mm is heated at a temperature lower than the sintering temperature and then sintered to produce the porous material. Therefore, it is required to prepare the alumina granules having a diameter in the range of from 0.5 to 1.5 mm and to pre-sinter the alumina granules. Further, the process is not suitable to produce a porous material of a larger size or a complicated shape since the compression pressure should be in the range from 1 to 4 tons/cm$^2$.

In the process described in the reference 2, the ceramic powder and the material which may be burnt off are mixed and compression molded together and then sintered into the porous material. Thus, it is impossible to selectively form the pores into a closed cell structure or an open cell structure, or to control sizes or directions of the pores since the position of the burnt-off material in the compressed material cannot be controlled.

SUMMARY OF THE INVENTION

It is, therefore, an object of the present invention to provide a process for production of a porous article characterized in that sizes and directions of pores can be controlled without any specific apparatus.

The present invention is based on the idea as follows:

When voids of a porous material having a controlled structure made of a heat decomposable material are filled with a slurry comprising ceramic powder, and sintered, it is possible to produce a porous material wherein the pore sizes and orientations are controlled.

According to the present invention, there is provided a process for the production of a ceramic porous shaped article, which process comprises filling voids of a porous material having a three dimensionally connected structure made of a heat decomposable material, in which structure, adjacent units share connecting portions and voids, with a slurry comprising ceramic powder, and then heating to sinter the porous material filled with the ceramic powder.

The present invention further provide, a process for the production of a ceramic shaped article having a porous layer on the surface thereof, which process comprises disposing a porous material having a three dimensionally connected structure made of a heat decomposable material, in which structure adjacent units share connecting portions and voids, in contact with or adjacent to a ceramic substrate, filling a space between the ceramic substrate and the porous material and filling the voids of the porous material with a slurry comprising ceramic powder made from the same material as the ceramic substrate, and then heating to sinter the porous material and the ceramic substrate together.

DETAILED DESCRIPTION OF THE INVENTION

The heat decomposable material used in the present invention may be heat-decomposed, burnt or sublimated to disappear at a temperature lower than the sintering temperature without leaving ash or leaving ash which is not harmful to a human being. For example, such a material may be a synthetic resin, a natural resin, a paraffin or a wax.

The porous material which is made of the heat decomposable material has a three dimensional structure in which the adjacent units share the connecting portions and the voids. Each unit may be in the form of a sphere, a particle, a polygon, a fiber or a more or less modified form thereof. These units are partly connected to each other to extend three dimensionally, thereby the voids are formed between the adjacent units such that the voids extend three dimensionally. The connection between the units may be carried out by any conventional means such as fusion and adhesion. The extent of the connection depends on the application of the porous material and can be easily determined from the intended average pore diameter and porosity. The porous material may consist of any number of layers comprising the units. Although it is preferred that the material consists of one to fifteen layers across the thickness the number of the layers is not limited to such a range.

When the porous article is used as an implant material, the number of layers across the thickness depends on the size of the implant, and it is preferably in the range of from 1 to 3 layers. When the number of the layers exceeds the above range, it is difficult to clean and sterilize an innermost portion of the porous material. The size of the unit is determined according to the pore size of the ceramic porous article. Usually the unit size is in the range of about from 0.01 to 2.5 mm, preferably in the range of about from 0.05 to 1.5 mm. In the case of the implant material, the unit size is preferably in the range of about from 0.05 to 1.5 mm. The diameter of the connecting portion is usually in the range of about from 0.01 to 0.5 mm. In the case of the implant material, the lower limits of the sizes of the unit and the connected portion may be determined such that an osteoblast can invade the pore of the implant material. The upper limits may depend on the strength of the material since a pore that is too large makes the material weak. The shape of the porous material may be selected according to the application of the material and may be in the form of a plate, a cylinder or a half sphere.

In another aspect of the present invention, the ceramic shaped article having the porous layer on the surface thereof is produced with the use of the ceramic substrate. The ceramic substrate may be made of a conventional ceramic material such as alumina, zirconia, calcium triphosphate, hydroxyapatite, silicon nitride, silicon carbide and so on. In the application as the implant material, it is preferable to use alumina, zirconia, calcium triphosphate or hydroxyapatite. The ceramic substrate is a shaped material having a desired shape or a sintered material after shaping. The slurry comprises ceramic powder, a binder and a dispersing medium.

The ceramic powder may be conventional ceramic powder such as alumina, zirconia, calcium triphosphate, silicon nitride, silicon carbide and so on. In the application as the implant material, alumina, zirconia, calcium triphosphate and hydroxyapatite are preferred since they are not harmful to the human body.

The particle size of the ceramic powder is preferably less than 5 $\mu$m and more preferably less than 1 $\mu$m. The smaller diameter is particularly preferred since the properties during the sintering and the dispersing stability can be improved. The combination of the binder and the dispersing medium can be selected such that they may substantially form a solution and any conventional combination can be used. For example, when the dispersing medium is water, polyvinyl alcohol, polyethylene oxide, hydroxyethyl cellulose and so on can be used. When the dispersing medium is a nonaqueous one, polyvinyl butyral, polymethyl methacrylate, cellulose acetate butyrate and so on can be used. The slurry can be produced through a conventional process in which the ceramic powder is well mixed in the binder solution and dispersed therein. The contents of the binder and the ceramic powder are important factors which determine the viscosity of the slurry.

The viscosity of the slurry should be low enough to be penetrated in the voids of the porous material having the three dimensionally connected structure. The viscosity can be determined by taking into account the size of the unit and the connected portion and may be in the range of from 5 to 1000 centipoise.

The content of the ceramic powder is preferably in the range of from 15 to 60% by weight and the content of the binder is preferably in the range of from 2 to 20% by weight based on the ceramic powder weight. However, since the viscosity of the slurry is determined by the combination of the ceramic powder and the binder, both the contents thereof are not limited to such ranges.

In the production of the ceramic porous article according to the present invention, any conventional forming process can be employed. For example, the process may comprise disposing the heat decomposable porous material in a mold, pouring the ceramic slurry into the mold, then drying or molding to obtain the shaped article, and heating the shaped article by the conventional way to burn off the binder and sinter the ceramic powder.

In the above case, the porous shaped article can be produced. However, in another aspect of the present invention, the composite shaped article in which the ceramic substrate and the porous material are bonded together firmly can be produced. In the application as the implant material, the product having such the structure is preferred in view of the strength thereof.

In the production of the composite article, the heat decomposable porous material is disposed such that it may contact the ceramic substrate or may be separated from the ceramic substrate by some distance. Then, the space portion between the porous material and the ceramic substrate and the voids in the porous material are filled with the slurry comprising the ceramic powder having the same quality as the ceramic substrate and then the slurry is dried to obtain the shaped article. Alternatively, with casting, the shaped material having a concave portion on the surface thereof is produced and then the porous material is disposed in the concave portion. With additional casting, the shaped material and the porous material is made integral. The resulting shaped article is heated using a conventional process to remove the binder and to sinter the article.

Thus, a ceramic porous article wherein pore size and orientation are controlled can be produced by filling the voids of the heat decomposable porous material having the predetermined structure with the slurry comprising the ceramic powder and then heating the porous material with the ceramic slurry to remove the heat decomposable material and to sinter the ceramic powder.

According to the process of the present invention, the shaped ceramic article can be easily produced without the use of any specific apparatus, wherein the pore size and orientation are controlled. Such a shaped ceramic article can be used in applications such as an implant material, a filter medium and so on.

In particular, when it is used as an implant material, a newly forming bone can penetrate into the porous structure after the material is embedded in the body, and the material exhibits excellent fixing properties with the bone due to the interlocking effect therebetween. Further, the implant material has high strength and also provides great improvement in sterilization and cleaning.

The present invention will be further explained with the reference t the following examples, in which "parts" means "parts by weight".

EXAMPLE 1

Polystyrene beads having an average diameter of 0.5 mm (ESBRIGHT (trade mark) beads T-8K" manufactured by Sumitomo Chemical Co., Ltd.) were supplied on a 1000 mesh wire cloth having a diameter of 35 mm placed on a glass filter such that the number of laminated layers was three. A mixed solvent of methyl ethyl ketone and ethanol (7:3 in volume ratio) was supplied in the glass filter so that the solvent might not disturb the layered structure. Immediately after the supply of the solvent, vacuum filtration was carried out. The procedures above were repeated twice. After allowed to dry, the polyethylene beads from the glass filter were connected to each other to form a porous block of 32 mm in diameter and 7 (?) mm in thickness, which block had the voids between the beads. The polystyrene porous block was disposed in a plaster mold of 32 mm in diameter, 15 mm in depth and 15 mm in thickness with plate paraffin, into which an alumina slurry having the following formulation was supplied and cast:

| | |
|---|---|
| Alumina (AKP-20 manufactured by Sumitomo Chemical Co., Ltd., 0.6μ in diameter) | 100 parts |
| Polyvinyl alcohol (degree of polymerization of about 500) | 2 parts |
| $Mg(NO_3)_2 \cdot 6H_2O$ | 0.3 part |
| Water | 67 parts |

After drying the slurry and removing from the mold, the block was heated at 500° C. to thermally decompose the polystyrene, and then further heated at 1600° C. for one hour to sinter the alumina powder. The resulted alumina porous article had spherical voids of 0.4 mm in diameter and the channels of from 0.04 to 0.06 mm in diameter connecting the voids.

EXAMPLE 2

A mold (50 mm×50 mm×10 mm) was prepared from glass plates. On the bottom, a piece of paper was disposed, on which polymethyl methacrylate beads having a diameter of 0.3 mm (SUMIPEX (trade mark) -B MH manufactured by Sumitomo Chemical Co., Ltd.) were supplied such that three layers were laminated. Chloroform solution containing 10% of polymethyl methacrylate was supplied in the polymer beads such that the uppermost beads were wetted uniformly and allowed to dry.

Removing the mold, polymethyl methacrylate beads formed a porous block as a whole, in which the beads were bonded each other and voids existed among the beads. The block had a size of 50 mm×50 mm×1 mm (thickness). The polymethyl methacrylate porous block was disposed in a plaster mold (50 mm×50 mm×10 mm thickness) with plateform paraffin. A hydroxyapatite slurry having the following formulation was supplied on the block and cast:

| | |
|---|---|
| Hydroxyapatite (0.05 to 2μ in diameter, Ca/P = 1.67) | 100 parts |
| Polyvinyl alcohol (degree of polymerization of about 500) | 2 parts |
| Water | 67 parts |

After drying and removing the mold, the block was heated at 350° C. to thermally decompose polymethyl methacrylate and then further heated at 1100° C. for one hour to sinter the hydroxyapatite powder. The resulted porous article had spherical voids of 0.25 mm in diameter and channels of from 0.03 to 0.05 mm in diameter which connected the voids.

EXAMPLE 3

The same alumina slurry as in Example 1 was supplied in a plaster mold (50 mm×70 mm×5 mm in depth) with a thickness of 15 mm to form a shaped article having a concave portion of 30 mm×50 mm×2 mm (thickness) in a central portion. Polystyrene porous article (30 mm×50 mm×2 mm in thickness) made of polystyrene beads having a diameter of 1 mm through the same procedure as in Example 1 was disposed in the concave portion and then the alumina slurry was supplied as in Example 1 and cast. After drying and removing the mold, a porous material of alumina was formed on a surface of a densely sintered material of alumina.

What is claimed is:

1. A process for the production of a ceramic shaped implant having a porous layer on the surface thereof, which process comprises:

disposing a porous element in contact with or adjacent to a ceramic substrate, wherein the element is made by filling voids in a layered structure of spherical units of heat decomposable material having a diameter of from 10 to 2500 μm with a solvent followed by removing the solvent and drying the structure, filling a space between the ceramic substrate and the porous element and filling the voids of the porous element with a slurry containing ceramic powder made from the same material as the ceramic substrate, and then heating to thermally decompose the decomposable material and to sinter the ceramic powder and substrate together to form said ceramic implant having a porous layer thereon with pores in the shape of said units.

2. The process according to claim 1 in which the ceramic powder is made of material selected from the group consisting of alumina, zirconia, calcium triphosphate and hydroxyapatite.

3. The process of claim 1, wherein said porous element comprises one to fifteen layers of said three dimensionally shaped spherical units.

4. The process of claim 1, wherein said porous element comprises one to three layers of said three dimensionallyshaped spherical units.

5. The process of claim 1, wherein the ceramic substrate is made of material selected from the group consisting of alumina, zirconia, calcium triphosphate and hydroxyapatite.

6. The process of claim 1, wherein the particle size of the ceramic powder is less than one micron.

7. The process of claim 1, wherein said slurry comprises a mixture of ceramic powder, binder and a dispersing medium and has a viscosity of from 5 to 1000 centipoise.

8. The process of claim 1, wherein the content of the ceramic powder in the slurry is from 15 to 60% by weight and the content of the binder is from 2 to 20% by weight based on the ceramic powder weight.

9. The process of claim 1, wherein the porous element is formed by using fusion or adhesion to connect said units in a three dimensional manner, said units being formed from a synthetic resin, natural resin, paraffin or wax.

10. The process of claim 1, wherein the units are in the form of beads formed from polystyrene or polymethyl methacrylate.

* * * * *